United States Patent [19]

Anderson

[11] Patent Number: 5,961,664
[45] Date of Patent: Oct. 5, 1999

[54] DIRECT HAIR DYE COMPOSITIONS AND METHODS CONTAINING NOVEL ANTHRAQUINONE MIXTURES

[75] Inventor: James S. Anderson, Bethel, Conn.

[73] Assignee: Bristol-Myers Squibb Company, New York, N.Y.

[21] Appl. No.: 08/889,987

[22] Filed: Jul. 10, 1997

[51] Int. Cl.⁶ .............................. A61K 7/13; C09B 1/16
[52] U.S. Cl. ................ 8/405; 8/428; 8/643; 552/255
[58] Field of Search .................. 8/405, 407, 428, 8/675, 643; 552/255

[56] References Cited

U.S. PATENT DOCUMENTS

| | | | |
|---|---|---|---|
| 2,321,767 | 6/1943 | Ogilvie | 552/245 |
| 2,727,045 | 12/1955 | McSheehy | 260/378 |
| 3,168,441 | 2/1965 | Bil et al. | 167/88 |
| 3,368,942 | 2/1968 | Kaiser et al. | 167/88 |
| 3,449,056 | 6/1969 | Pum et al. | 8/10.1 |
| 3,703,350 | 11/1972 | Buecheler et al. | 8/675 |
| 3,881,865 | 5/1975 | Greenhalgh et al. | 8/675 |
| 4,834,768 | 5/1989 | Grollier | 8/405 |
| 4,835,314 | 5/1989 | Konrad et al. | 564/441 |
| 4,886,517 | 12/1989 | Bugaut | 8/416 |
| 4,921,504 | 5/1990 | Clausen et al. | 8/415 |
| 5,030,241 | 7/1991 | Clausen et al. | 8/414 |
| 5,037,446 | 8/1991 | Konrad et al. | 8/414 |
| 5,112,359 | 5/1992 | Murphy et al. | 8/405 |
| 5,169,403 | 12/1992 | Chan et al. | 8/405 |
| 5,226,924 | 7/1993 | Junino et al. | 8/405 |
| 5,314,505 | 5/1994 | Chan et al. | 8/426 |
| 5,360,930 | 11/1994 | Chan et al. | 564/284 |
| 5,486,629 | 1/1996 | Chan et al. | 552/236 |
| 5,520,707 | 5/1996 | Lim et al. | 8/426 |
| 5,688,291 | 11/1997 | Said et al. | 8/405 |

FOREIGN PATENT DOCUMENTS

| | | |
|---|---|---|
| 4031342 | 4/1992 | Germany . |
| 210734 | 10/1940 | Switzerland . |
| 92/06670 | 4/1992 | WIPO . |

OTHER PUBLICATIONS

Chemical Abstracts, American Chemical Society, vol. 35, Editor: E. J. Crane, p. 1941; col. 5721.; Abstract: Sulfuric acid ester of 1–y–hydroxypropylamino– 4–β–hydroxyethylaminoanthorquinone. Soc. Pour l'ind. Chim. a Bale. Swiss 210,734, Oct. 16, 1940.

*Primary Examiner*—Yogendra Gupta
*Assistant Examiner*—Caroline D. Liott
*Attorney, Agent, or Firm*—Morton S. Simon; Charles J. Zeller

[57] ABSTRACT

An anthraquinone mixture comprising three 1,4-hydroxyalkylamino-anthraquinone derivatives, wherein two of the anthraquinone compounds in the mixture are symmetric and the other anthraquinone compound is asymmetric, and wherein each of the anthraquinone compounds has similar polarities. The anthraquinone mixtures are used in compositions and methods for the direct dyeing of keratinous fibers, particularly human hair on the head.

11 Claims, No Drawings

DIRECT HAIR DYE COMPOSITIONS AND METHODS CONTAINING NOVEL ANTHRAQUINONE MIXTURES

FIELD OF THE INVENTION

The invention relates generally to compositions and methods for preparing directly acting, semipermanent hair dyes that result in true color and do not adversely affect the texture and condition of the hair after application. The present invention more particularly relates to hair coloring compositions and methods comprising novel anthraquinone ("AQ") dyes in addition to other additives and components typically used in semipermanent hair dye formulations.

BACKGROUND OF THE INVENTION

Direct dye colorants are essential elements in hair coloring preparations for the semi-permanent dyeing of keratin fibers, such as human hair. In contrast to oxidation dyes which are conventionally developed with the aid of oxidizing agents, such as hydrogen peroxide, directly acting dyes color hair on their own, without oxidizing agents, at room temperature. Unlike oxidative dyes, semi-permanent or direct dyes advantageously do not cause the appearance of a demarcation or borderline phenomenon between the ends and half-lengths of the hair and the growing roots of the hair.

A direct dye composition for the semi-permanent coloring of hair should optimally serve to cover gray hair and to apply a new color to hair of any color. The dyed hair should be resistant to fading due to light or friction, e.g., rubbing. Semipermanent dyes should be toxicologically benign. They should be resistant to change in the hue or color if another substance is applied to the hair, such as a permanent wave and the like.

The commercially available colorant Disperse Blue 3 (DB 3) is a widely used semi-permanent hair colorant. It is actually a mixture of three blue anthraquinones, Disperse Blues 3, 14 and 23 (i.e., DB 3, DB 14 and DB 23). The mixture of DB 3, DB 14 and DB 23 is produced during the manufacture of commercially available colorant DB 3, which is synthesized by reacting quinizarin (i.e., 1,4-dihydroxyanthraquinone), or leucoquinizarin, with a mixture of 2-aminoethanol and methylamine (Ventkataraman, K., 1952, The Chemistry of Synthetic Dyes, Vol. II, Academic Press Inc., New York, p. 809; Abrahart, E. N., 1968, Dyes and their Intermediates, New York: Pergamon Press, New York, p. 176) as represented hereinbelow:

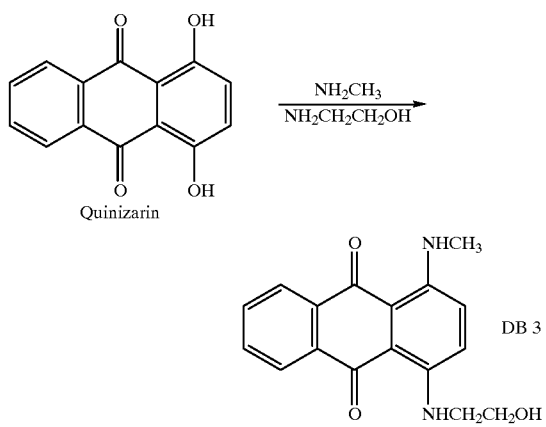

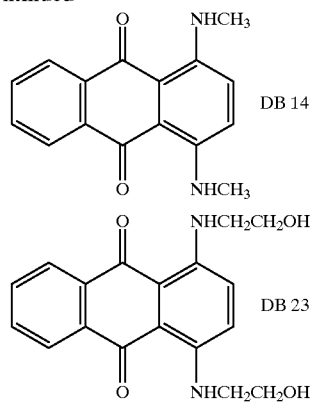

As those having skill in the art will appreciate, the technical name of the specific DB 3 anthraquinone is 1-[(2-hydroxyethyl)amino]-4-(methylamino)-9,10-anthracenedione (International Cosmetic Ingredient Dictionary, Monographs, Sixth Edition, Eds., J. A. Wenniger and G. N. McEwen, Jr., The Cosmetic, Toiletry and Fragrance Association (CTFA), Washington, D.C., 1995, pages 350–351). DB 23 is chemically known as 1,4-bis[(2-hydroxyethyl)amino]-9,10-anthracenedione, and DB 14 is chemically known as 1,4-bis(methylamino)-9,10-anthracenedione.

The mixture of different anthraquinones comprising the commercially available colorant DB 3 has been shown to be efficacious as a hair dye due to the synergistic effect of the presence of multiple anthraquinones in the mixture (Ventkataraman, K., 1952, Ibid.). However, as a direct result of the nature of the commercially available colorant DB 3 as a mixture, it has several disadvantages in hair coloring formulations. One disadvantage is the potential batch-to-batch variations in the DB 3: DB 14: DB 23 ratios contained in a product comprising the commercially available colorant DB 3; such variations are likely to affect hair dyeing properties. Another disadvantage is manufacturer-to-manufacturer variation in the ratios of the component anthraquinones (Bide, M. J. & McConnell, R. L., Textile Chemist and Colorist 28(3):14, 1996), which result in different compositions (see Table 1) and different dyeing properties. A further disadvantage is that different manufacturers may add toners of various colors, such as Disperse Violet 1 (DV 1), i.e., 1,4-diaminoanthraquinone, (Table 1); such toners will also change dyeing results. Also, the use of the mixture comprising DB 3 makes quantitative analysis quite difficult, since a chromatographic separation to resolve components and at least three quantifications are routinely necessary.

TABLE 1

| Compositions of commercially-available DB 2 samples analysed by HPLC* | | |
|---|---|---|
| | Artisil Blue B (Sandoz Corp.) | Intrasperse Brilliant Blue B Supra (Crompton & Knowles Corp.) |
| DB 3 | 30.7% | 28.6% |
| DB 14 | 9.1% | 4.4% |

TABLE 1-continued

Compositions of
commercially-available DB 2 samples analysed by HPLC*

| | Artisil Blue B (Sandoz Corp.) | Intrasperse Brilliant Blue B Supra (Crompton & Knowles Corp.) |
|---|---|---|
| DB 23 | 14.2% | 17.3% |
| DV 1 | 0% | 11.3% |

*The remainder of the samples are other colored components and colorless dispersants.

Thus, it would be an improvement and an advantage in the art to have a direct hair coloring product containing anthraquinone dyes for darker and more intense coloring of hair, but which avoid the above-listed disadvantages that are associated with the use of known anthraquinone mixtures in hair coloring compositions.

The use of 1,4-di(mono-or poly)hydroxyalkylamino-9, 10-anthraquinones for the dyeing of hair is disclosed in U.S. Pat. No. 5,226,924 to A. Junino et al. The synthesis and use of specific mixtures of anthraquinones are not described. The anthraquinone dye(s) that are disclosed by Junino et al. specifically require a 2,3-dihydroxypropylamino group at position 4 of the molecule.

U.S. Pat. No. 3,368,942 to W. J. Kaiser et al. discloses water soluble aminoanthraquinone hair dyes, but is silent regarding specific anthraquinone mixtures as described by the present invention.

U.S. Pat. No. 4,834,768 to J. F. Grollier discloses dyeing compositions for the direct coloring of hair which comprise, among other dyestuffs, anthraquinones and which require the use of a xanthan gum.

Patents which disclose anthraquinone dyes for hair dyeing are U.S. Pat. No. 3,168,441 to M. Bil et al.; U.S. Pat. No. 3,449,056 to F. Pum et al.; U.S. Pat. Nos. 5,486,629; 5,360,930; 5,169,403; 5,314,505 to A. Chan et al.; U.S. Pat. No. 5,112,359 to B. Murphy et al.; and U.S. Pat. No. 5,520,707 to M.-I. Lim et al. None of these patents disclose the novel anthraquinone dye mixtures having enhanced dyeing properties and improved color intensity when used with other dyes as described by the present invention.

DE 4,031,342 discloses 1,4-bis-(hydroxyalkyl)amino anthraquinones, but does not teach or disclose particular mixtures of anthraquinones having chemical structures described for the anthraquinone components of the present invention.

The use of anthraquinone dyes such as DB 23 in the dyeing of synthetic fibers, e.g., polyolefin fibers, has been described, for example, in U.S. Pat. Nos. 2,199,813 and 3,235,322, but is clearly distinguished from the use of anthraquinone dyes in compositions for the coloring of keratinous fibers, such as animal and human hair. 1,4-diaminoanthraquinone disperse dyes have also been disclosed, in an unrelated field of art, for use on synthetic polymer substrates such as cellulose acetates, nylons and polyesters (R. S. Sinclair et al., 1975, *J.S.D.C.*, 91:399–405.

The blue anthraquinone DB 23 has been disclosed in U.S. Pat. Nos. 4,835,314, 4,921,504, 5,030,241 and 5,037,446, but is used in each as the sole anthraquinone dye in the dye formulations. The foregoing patents do not disclose DB 23 as a component of novel anthraquinone mixtures having stronger synergistic effects than does DB 3 when used with other anthraquinones, such as Disperse Violet 1, in the dyeing of human hair.

The anthraquinone compounds and mixtures of the present invention are distinct from prior art hair dyeing compounds and offer surprising and advantageous hair coloring properties after use.

SUMMARY OF THE INVENTION

It is an object of the invention to provide direct dye compositions for the semipermanent dyeing of keratinous fibers, including animal and human hair, with particular regard to human hair. The compositions of the invention comprise novel mixtures of anthraquinones comprising three anthraquinone components. The compositions further comprise other components conventionally used in such semi-permanent dye formulations. Methods employing the compositions as direct dyes are also provided by the present invention.

It is another object of the invention to provide novel anthraquinone mixtures having less batch-to-batch and manufacturer-to-manufacturer variation than the commercially available DB 3 colorant. In accordance with the present invention, the hair coloring capacity of the novel anthraquinone dye mixtures is strong, intense and lasting.

Yet another object of the present invention is to provide novel anthraquinone dye mixtures, as described, which demonstrate a surprisingly and unexpectedly stronger synergistic dyeing effect than does conventionally known DB 3 when the anthraquinone dye mixtures of the present invention are used alone or in combination with other anthraquinones routinely employed in hair dyeing, for example, Disperse Violet 1.

Further objects and advantages afforded by the invention will be apparent from the detailed description hereinbelow.

DETAILED DESCRIPTION OF THE INVENTION

The present invention provides new anthraquinone dyes, more preferably novel mixtures of anthraquinones, for the direct dyeing of hair, in particular, for the semipermanent coloring of human hair. In accordance with the present invention, the new anthraquinone mixtures were surprisingly found to color hair more intensely than does commercially available DB 3 or DB 23.

In accordance with the present invention, the novel anthraquinone dye mixtures contain three blue anthraquinones having the general formula as shown below:

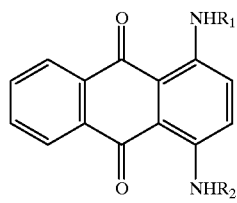

wherein $R_1$ and $R_2$ are, independently, monohydroxy $C_2$–$C_6$ alkyl, straight chain or branched chain, with the proviso that in two of the anthraquinones, $R_1$ and $R_2$ are the same, and as a consequence, such anthraquinones are symmetric, and in the third of the anthraquinones, $R_1$ and $R_2$ differ, and as a consequence, such an anthraquinone is asymmetric.

In accordance with the present invention, the novel anthraquinone mixtures are prepared by reacting quinizarin with two amines, preferably primary monohydroxyalkylamines, in which each amine has one substituent group, namely, a monohydroxyalkyl group, linear or branched. The alkyl is preferably a $C_2$–$C_6$ alkyl. For example, to synthesize mixtures of anthraquinones according to the present invention, an amine mixture such as $NH_2R_1 + NH_2R_2$ is used, wherein $R_1$ and $R_2$ are as defined above.

Examples of suitable hydroxyalkylamines for use in synthesizing the AQ mixtures of the present invention include but are not limited to, 1-amino-2-propanol, 3-aminopropanol and 2-aminoethanol. In addition, all isomers of aminobutanol, aminopentanol and aminohexanol can be employed in synthesizing the mixtures of the present invention, provided that the amine is a primary amine. The synthesis of the anthraquinone mixtures of the present invention is similar to the synthesis scheme presented hereinabove for the DB 3 preparation.

The present invention embodies several different anthraquinone mixtures as described and illustrated hereinbelow. Mixture 1 in accordance with the present invention is prepared, as shown in reaction scheme A, by treating quinizarin with 2-aminoethanol and 3-aminopropanol. Mixture 1 comprises three different anthraquinone components, namely, DB 23; 1-[(2-hydroxyethyl)amino-4-[(3-hydroxypropyl)amino]-9,10-anthracenedione (1); and 1,4-bis[(3-hydroxypropyl)amino]-9,10-anthracenedione (2).

A second and distinctive mixture, Mixture 2, is prepared in accordance with the present invention, as shown in reaction scheme B, by treating quinizarin with 2-aminoethanol and 1-amino-2-propanol and comprises three different anthraquinone components, namely, DB 23; 1-[(2-hydroxyethyl)amino]-4-[(2-hydroxypropyl)amino]-9,10-anthracenedione (3); and 1,4-bis[(2-hydroxypropyl)amino]-9,10-anthracenedione (4).

In Mixture 2, 1-[(2-hydroxyethyl)amino]-4-[(2-hydroxypropyl)amino]-9,10-anthracenedione, i.e., component (3), is a novel compound produced in accordance with the present invention. Component (3) was separated from the other anthraquinone components in the mixture employing reverse phase high pressure liquid chromatography. The chromatography conditions used were a Bondclone chromatography column (150×3.9 mm); a mobile phase of acetonitrile/water, 75:25 (v/v); a flow rate of 1.5 ml/minute and a column temperature of 25° C. Detection of the separated sample component peaks was performed at 260/635 nm. The elution times for the respective components of Mixture 2 are as follows: 5.9 minutes for DB 23; 8.5 minutes for novel compound (3) and 12.8 minutes for compound (4). As will be appreciated by those skilled in the art, the discrete anthraquinone compounds can be isolated, for example, by collecting the eluate material at the appropriate time of elution and removing the

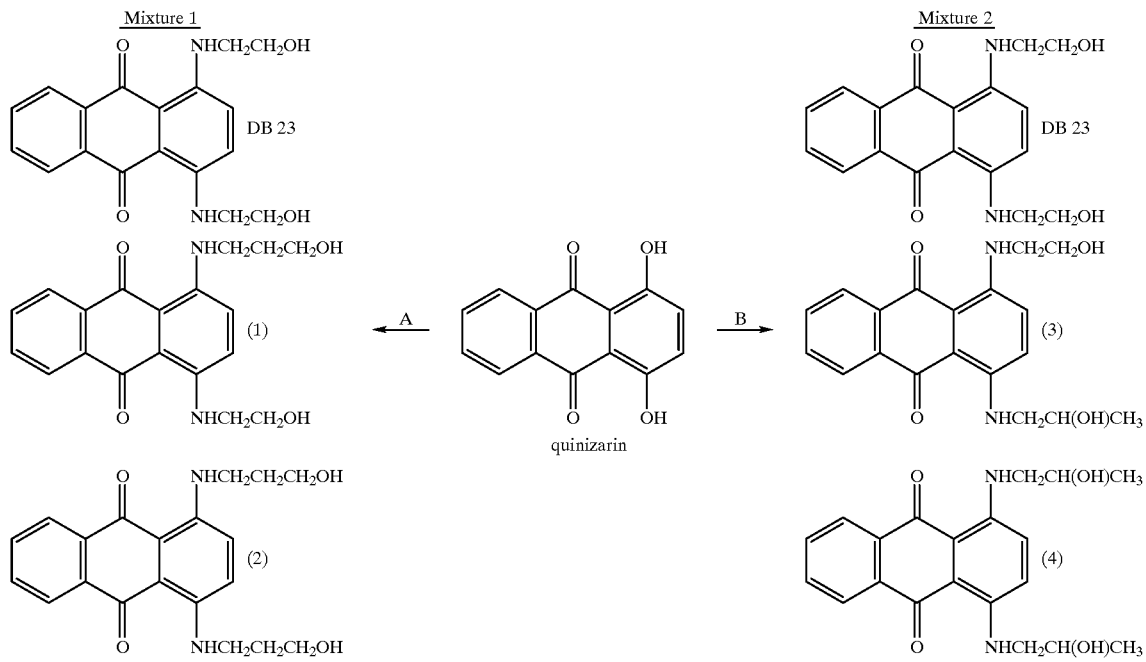

solvent in vacuo, using routine procedures known in the art.

The liquid chromatography conditions described for separating and isolating the anthraquinone compounds comprising Mixture 2 were also used to separate the three anthraquinone components comprising Mixture 1. The elution times for the respective components of Mixture 1 are as follows: 5.9 minutes for DB 23; 8.2 minutes for compound (1) and 11.6 minutes for compound (2).

A third and distinctive mixture of the present invention, Mixture 3, is prepared, as shown by reaction scheme C, by treating quinizarin with 1-amino-2-propanol and 3-aminopropanol as depicted hereinbelow. Mixture 3 comprises three different anthraquinone components, namely, 1,4-bis[(2-hydroxypropyl)amino]-9,10-anthracenedione (4); 1-[(2-hydroxypropyl)amino]-4-[(3-hydroxypropyl)amino]-9,10-anthracenedione (5); and 1,4-bis[(3-hydroxypropyl)amino]- 9,10-anthracenedione (2).

For example, in an anthraquinone mixture of the present invention, the asymmetric anthraquinone (e.g., compound (1) in Mixture 1 and compound (3) in Mixture 2) can comprise about 10% to 70% of the total mixture, and the combined symmetric anthraquinones (e.g., DB 23 and compound (2) in Mixture 1, and DB 23 and compound (4) in Mixture 2) can comprise about 30% to about 90% of the total mixture.

In accordance with the present invention, a more preferred mixture comprises about 25% to about 65% of the asymmetric anthraquinone and about 3% to about 70% of each of the symmetric anthraquinone compounds. A most preferred mixture comprises about 30% to about 60% of the asym-

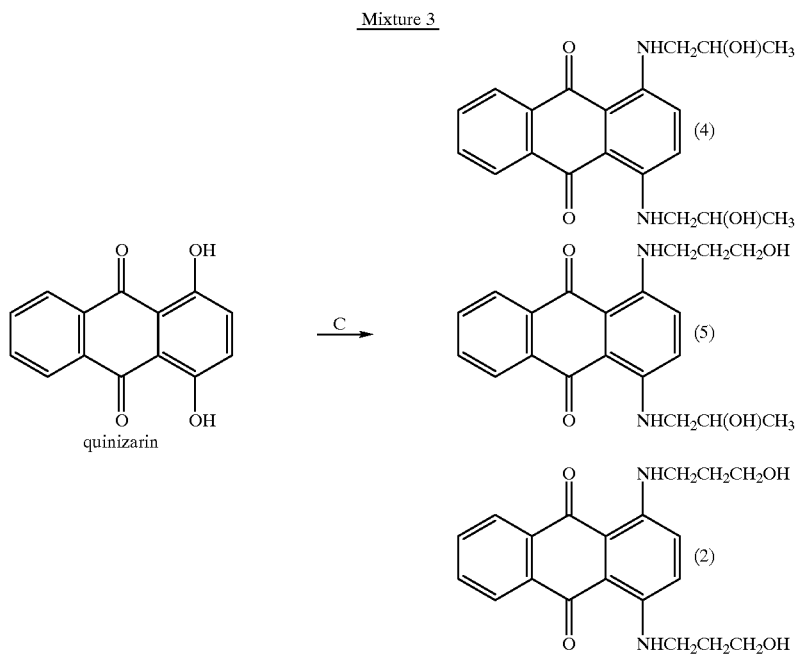

Mixture 3

The relative proportions of each of the anthraquinone components in the anthraquinone mixtures of the present invention will vary and can be controlled by the proportions of the two amines used in the synthesis of the mixtures. Notwithstanding, the mixtures contain three anthraquinone components. The anthraquinone mixtures of the present invention further comprise both asymmetric and symmetric anthraquinone components. For example, in Mixture 1, compound (1) is asymmetric, while DB 23 and compound (2) are each symmetric. In Mixture 2, compound (3) is asymmetric, while DB 23 and compound (4) are each symmetric. Similarly, in Mixture 3, compound (5) is asymmetric, while compounds (4) and (2) are each symmetric.

The two symmetric anthraquinone compounds may be present in the mixtures of the present invention in equal or unequal concentrations and, preferably, each can comprise about 1% to about 80% by weight, based on the total weight of the mixture. The asymmetric anthraquinone preferably comprises about 10% to 70% by weight, based on the total weight of the mixture.

It is to be understood that, unless otherwise specified, the concentrations of the component ingredients in the mixtures and/or compositions of the present invention are in % by weight (w/w), based on the total weight of the mixture or composition.

metric anthraquinone and about 5% to about 50% of each of the symmetric anthraquinone compounds.

The anthraquinone components which comprise each of the mixtures of the present invention have very similar polarities, and thus should not have the above-mentioned disadvantages of batch-to-batch and manufacturer-to-manufacturer variations in dyeing that are associated with the use of the commercially available DB 3 colorant. For example, use of standard thin layer chromatography conditions to separate the three components of commercially available DB 3 (e.g., 9:1 chloroform:methanol on a silica support) does not separate the components of Mixture 1 of the present invention at all, and scarcely separates the components of Mixture 2 of the present invention. These results demonstrate the close polarities of the components in each of the anthraquinone mixtures of the present invention versus the disparate polarities of the different components of commercially available DB 3. As a consequence of the similarities in the polarities of the components of the novel anthraquinone mixtures of the present invention (as illustrated by Mixtures 1, 2 and 3), variations in the ratios of these components are expected to have virtually no effect on dyetake. In contrast, this improved attribute of the mixtures of the present invention is not realized with commercially available DB 3.

In accordance with an embodiment of the present invention, the direct dye mixtures, as described, are formulated into compositions for the semipermanent coloring of keratinous fibers, including human or other hair. The compositions comprise tinctorially effective amounts of the anthraquinone mixtures of the invention in a cosmetically acceptable vehicle as further described hereinbelow.

In practice, the novel anthraquinone mixtures of the present invention are most often used in combination with one or more other conventionally-known dye compounds that are used in direct hair dye formulations. A variety of such direct dyeing colorants are known and include nitro dyes, azo dyes or other anthraquinone dyes, and the like. The admixture of the dyes of the present invention with additional dyes provides the desired color or shade. The amount of each dye used depends upon the lightness or darkness of the desired shade, as well as on the desired tonality. Advantageously, the anthraquinone mixtures according to the present invention provide intense color and sufficient affinity for adhering to hair. Nonlimiting examples of the variety of dye components suitable for use in formulating hair dye compositions in combination with the anthraquinone mixtures of this invention include the following:

Yellow/Orange: Acid Orange 3, Disperse Orange 3, Disperse Black 9, HC Orange 1, HC Orange 2, HC Orange 3, HC Yellow 2, HC Yellow 4, HC Yellow 5, HC Yellow 6, HC Yellow 7, HC Yellow 9, HC Yellow 10, HC Yellow 11, HC Yellow 12, HC Yellow 13, HC Yellow 14, HC Yellow 15, 4-nitro-o-phenylenediamine, 2-nitro-5-glyceryl methylaniline, 4-nitrophenyl aminoethylurea, hydroxyethyl-2-nitro-p-toluidine, 3-methylamino-4-nitrophenoxyethanol, 2-amino-6-chloro-4-nitrophenol, 2-chloro-6-ethylamino-4-nitrophenol, Basic Yellow 57, Solvent Orange 45, 4-nitro-m-phenylenediamine, Natural Orange 6, 2-hydroxyethylamino-5-nitroanisole, 2-amino-3-nitrophenol, 6-nitro-o-toluidine, N-ethyl-3-nitro PABA, N-hydroxyethyl-2,6-dinitro-p-anisidine, 6-nitro-2,5-pyridinediamine and 4-chloro-5-methyl-2-nitrophenol.

Preferred for use among the yellow/orange dyes are: Acid Orange 3, Disperse Orange 3, Disperse Black 9, HC Orange 1, HC Yellow 2, HC Yellow 4, HC Yellow 5, HC Yellow 6, HC Yellow 7, HC Yellow 9, HC Yellow 10, HC Yellow 12, HC Yellow 14, HC Yellow 15, 4-nitro-o-phenylenediamine, 2-nitro-5-glyceryl methylaniline, 4-nitrophenyl aminoethylurea, hydroxyethyl-2-nitro-p-toluidine, 3-methylamino-4-nitrophenoxyethanol, 2-amino-6-chloro-4-nitrophenol, 2-chloro-6-ethylamino-4-nitrophenol and Basic Yellow 57.

Red-Orange/Red: HC Red 1, HC Red 3, HC Red 7, HC Red 10, HC Red 11, HC Red 13, HC Red 14, 2-nitrophenylenediamine, 3-nitro-p-hydroxyethylaminophenol, 4-hydroxypropylamino-3-nitrophenol, 4-amino-3-nitrophenol, picramic acid, N-(2-hydroxyethyl)picramic acid, Basic Red 76, Disperse Red 17, N-methyl-3-nitro-p-phenylenediamine, 2-chloro-5-nitro-N-hydroxyethyl-p-phenylenediamine, 4-amino-2-nitrodiphenylamine-2'-carboxylic acid and 4-amino-4'-dimethylamino-2-nitrodiphenylamine-2'-carboxylic acid.

Preferred for use among the red-orange/red dyes are: HC Red 1, HC Red 3, HC Red 7, HC Red 10, HC Red 11, 2-nitro-p-phenylenediamine, 3-nitro-p-hydroxyethylaminophenol, 4-hydroxypropylamino-3-nitrophenol, 4-amino-3-nitrophenol, picramic acid and Basic Red 76.

Violet: Disperse Violet 1, Disperse Violet 4, HC Blue 2, HC Blue 6, HC Blue 9,HC Blue 10, HC Blue 11, HC Blue 12, HC Violet 1, HC Violet 2, N,N'-bis(2-hydroxyethyl)-2-nitro-p-phenylenediamine, 2-nitro-4-[bis(2-hydroxyethyl)amino] diphenylamine and Basic Violet 14.

Preferred for use among the violet dyes are: Disperse Violet 1, HC Blue 2, HC Blue 12, HC Violet 2, and Basic Violet 14.

Blue: Disperse Blue 1, Disperse Blue 3, Basic Blue 7, Basic Blue 9, Basic Blue 17, Basic Blue 26 and Basic Blue 99.

Preferred for use among the blue dyes are: Disperse Blue 1, Disperse Blue 3, Basic Blue 9, Basic Blue 7, Basic Blue 26 and Basic Blue 99.

Brown/Black: Basic Brown 16, Basic Brown 17 and Acid Black 1.

Preferred for use among the brown/black dyes are: Basic Brown 16 and Basic Brown 17.

In accordance with the present invention, the anthraquinone mixtures, and compositions thereof, may optionally include one or more dispersing agents, such as lignosulfates. When used, the dispersing agent(s) may be present in the mixture or composition at about 30% to about 70%, by weight.

The compositions of the present invention may also be formulated to include other conventionally used cosmetic components including, but not limited to, solvents, surface-active agents, thickeners, antioxidants, preservatives, fragrances, humectants and other ingredients typically employed in hair dye formulations as further described hereinbelow. Particularly useful are those materials or agents which may render the product more aesthetically appealing, such as fragrances, protein hydrolysates, vitamins and plant extracts. Examples include chamomile, eucalyptus oil, aloe vera, ginseng and pro-vitamin B.

The dye compositions according to the present invention may be formulated at alkaline, acidic, or neutral pH, at a pH range of about 5 to 12, and preferably from about 6 to 11. The appropriate pH may be adjusted with a suitable pH modifying agent which does not introduce toxicity under its conditions of use.

When the compositions of the present invention are to be alkaline, an alkalizing agent can be employed over a wide concentration range, depending on the dye and the particular alkalizing agent used, as well as the desired pH. Illustratively, the weight percent of the alkalizing agent can vary from 0% to about 10%, preferably from about 0.05% to about 5% and most preferably from about 0.10% to about 3%. Any of a wide variety of alkalizing agents can be used to adjust the pH of the present dyeing compositions on the basic side, provided that such agents do not interact chemically with the dye(s) employed, do not precipitate the dye(s), and are noninjurious and nontoxic to the scalp. Ammonium hydroxide or aqueous ammonia, because of their freedom from toxicity over a broad concentration range and their economy, are acceptable alkalizing agents. However, other nonlimiting examples of alkalizing agents that can be used in place of, or in combination with, ammonia or any other compatible ammonia derivative, include alkyl amines, e.g., monoethylamine, diethylamine, dipropylamine or triethylamine; an alkanediamine, e.g., 1,3-diaminopropane; the mono-, di- and tri-alkanolamines, e.g., monoethanolamine, diethanolamine, triethanolamine, 2-amino-2-methylpropanol and 2-amino-2-methyl-1,3-propanediol; polyalkylene polyamines, e.g., diethylenetriamine; or heterocyclic amines, e.g., morpholine, piperidine, 2-pipecoline, and piperazine. Combinations and mixtures of the above agents are also suitable for use.

Acidifying agents that may be used include inorganic or organic acids and acid salts such as sulfuric acid, formic acid, oleic acid, lactic acid, acetic acid, tartaric acid, phosphoric acid, hydrochloric acid and citric acid, as nonlimiting examples. Other pH adjusting agents for use include ammonium sulfate, sodium dihydrogen phosphate or potassium bisulfate. Illustratively, the amount of acidifying agent present is from about 0% to about 5%, preferably from about 0.05% to about 1%. In addition, the compositions of the present invention may contain buffering agents which maintain the pH within a particular and/or desired range. Collectively, the alkalizing, acidifying and buffering agents used in the compositions of the present invention are referred to as pH modifiers.

As is appreciated by those having skill in the art, the semi-permanent dyeing compositions of the present invention may also contain various customary adjuvants or additives such as fragrance, perfumes, sequestering agents, film-forming products and hair treating agents, dispersing agents, surfactants, hair conditioning agents, emulsifiers, chelating agents, preserving agents, opacifiers, humectants, antimicrobial agents and anti-oxidizing agents, as well as any other adjuvant routinely used in cosmetic compositions, and as further described herein. Typically, such additives, when used, will be present in quantities ranging from about 0.01% to about 60%, more preferably about 0.5% to about 55%.

Common chelating agents that can be employed in the compositions of the invention include the salts of ethylenediaminetetraacetic acid (EDTA), nitrilotriacetic acid, phosphates, pyrophosphates and zeolites.

Surface active agents, i.e., surfactants, that can be formulated into the direct dye compositions of the present invention include anionic, cationic, nonionic or amphoteric surfactants or mixtures thereof. Examples of suitable types of surface active agents include, but are not limited to, higher alkylbenzene sulfonates; alkylnapthalenesulfonates; sulfonated esters of alcohols and polybasic acids; taurates; fatty alcohol sulfates; sulfates of branched chain or secondary alcohols; alkyldimethylbenzylammonium chlorides; salts of fatty acids or fatty acid mixtures; N-oxyalkylated fatty acid alkanolamides and the like.

Illustrative of specific surfactants that can be used in the present invention are the following: sodium lauryl sulfate; polyoxyethylene lauryl ester; myristyl sulfate; glyceryl monostearate; triethanolamine oleate; sodium salt of palmitic methyl taurine; cetyl pyridinium chloride; lauryl sulfonate; myristyl sulfonate; lauric diethanolamide; polyoxyethylene stearate; ethoxylated oleyl diethanolamide; polyethylene glycol amides of hydrogenated tallow; stearyldimethyl benzyl ammonium chloride; dodecylbenzene sodium sulfonate; triethanolamine salt of p-dodecylbenzene sulfonate; nonylnaphthalene sodium sulfate; dioctyl sodium sulfosuccinate; sodium N-methyl-N-oleyl taurate; oleic acid ester of sodium isothionate; sodium dodecyl sulfate and the like. The quantity of surface active agent can vary over a wide range, such as from about 0.05% to about 15% and preferably from about 0.10% to about 5%.

Suitable thickening agents that may optionally be added to the compositions of the present invention include one or more of those which are commonly used in hair dyeing. More particularly, illustrative nonlimiting examples are products such as sodium alginate or gum arabic, guar gum, xanthan gums or cellulose derivatives, such as methylcellulose, e.g., Methocel 60HG or the sodium salt of carboxymethylcellulose, or hydroxyethylcellulose, e.g., Cellosize QP-40. Also suitable for use are acrylic acid polymers, such as polyacrylic acid sodium salt. In addition, inorganic thickening agents such as bentonite may be used. The thickeners are used alone or in admixture and the quantities can vary over a wide range, such as from about 0.1% to about 20%. Ordinarily, the quantity of thickener in the present compositions will range from about 0.5% to 5%.

The viscosity of the composition may vary from about 1 cp to about 100,000 cp. For a typical lotion formulation, the viscosity of the composition is between about 100 cp to about 10,000 cp.

Antioxidants that may also be incorporated into the present dye compositions include a variety of compounds which are known and conventionally used in the art for this purpose. Among the suitable antioxidants are the inorganic sulfites, e.g., sodium sulfite, thioglycollic acid and other mercaptans; butylated hydroxytoluene (BHT); sodium dithionite; various forms of ascorbic acid and its derivatives, for example, sodium ascorbate, erythorbic acid, ascorbyl palmitate, ascorbyl laurate, and the like. The quantity of antioxidant, when used, can vary appreciably. In general, however, the amount of antioxidant will be of the order of about 0.001% to about 1%.

Conditioners that can be incorporated into the compositions of the present invention include, but are not limited to, encapsulated silicones; silicones, such as amino functional and carboxy silicones; volatile silicones; combinations of a plant extract and a polypeptide; dimethyl dialkyl ammonium chloride (DMDAAC/acrylic acid type polymer) and a dialkyl quaternary ammonium compound in which the alkyl groups are $C_2$–$C_{16}$. Other well-known conditioners, such as lanolin, glycerol, oleyl alcohol, cetyl alcohol, mineral oil and petrolatum, can also be incorporated.

As described, the novel anthraquinone mixtures are formulated into the compositions of the present invention in tinctorially effective amounts, i.e., in concentrations which are adequate to color the hair. These quantities can vary over a wide range, but in general they will constitute from about 0.001% to greater than about 5%, for example, 10%. Preferably, the dyes will comprise from about 0.05% to about 5%, more preferably about 0.1% to about 3% of the composition.

For their application, the compositions according to the present invention may comprise water as a suitable carrier, which is usually the major constituent of the composition. The amount of water can vary over a wide range, depending in large part on the quantities of the other additives employed in the compositions. Accordingly, the water content can be as little as about 10%, but preferably will be from about 70% to about 99% of the hair dye composition.

In accordance with the present invention, the dyeing compositions are preferably aqueous. The term aqueous composition as used herein has its usual general sense as embracing any water-containing composition useful for the present purposes. This includes true solutions of the dye in aqueous medium, either alone or in conjunction with other materials or additives which are also dissolved or dispersed in the aqueous medium. The aqueous dye compositions of the present invention also encompasses any mixture of dye with the aqueous medium either alone or together with other ingredients. The dye may be colloidally dispersed in the medium or may be intimately mixed therein.

Further, the aqueous medium may comprise water, or water and an additional or auxiliary cosmetically acceptable organic solvent. The latter may be employed as a common solvent to enhance the solubility of the dye or some other organic material. Other auxiliary solvents that are suitable for this purpose include, but are not limited to, ethanol, carbitol, benzyl alcohol, phenylethyl alcohol, isopropanol; or glycols or glycol ethers, for example, propylene glycol, ethylene glycol, butylene glycol, diethylene glycol, dipropylene glycol, diethylene glycol monoethyl ether, glycerin and the like. The concentration of these organic solvents in the compositions of the invention is generally, for example, between about 0.5% and 20%, and preferably about 2 to 10% of the composition.

The compositions in accordance with the present invention can be provided in various conventional formulations for the treatment of keratinous fibers and for achieving the dyeing of hair. Typically, the novel anthraquinone dye mixtures of the present invention, or combinations thereof, are incorporated in a liquid hair dye vehicle of the type suitable for applying direct dyeing dye substances to the hair. A variety of such vehicles are known and appreciated by those in the art. These may vary from simple aqueous solutions and/or suspensions of the dye to very sophisticated aqueous compositions or thickened or gelled liquids, such as creams, foams, mousses, lotions, pastes, gels, and the like. Often, as described, the anthraquinone mixtures of the present invention are formulated in cosmetically acceptable vehicles which contain a second dye or blend of other dyes, nonionic, anionic or cationic surfactants, solvents, thickeners, antioxidants, preservatives, fragrances, etc. In such aqueous compositions, the carriers or vehicles may be water or a combination of water with other solvents, e.g., ethanol or polyethylene glycol. The dyes of the present invention may also be formulated as aerosols in aerosol systems, e.g., an aerosol emulsion system in which the dye or dye mixtures are contained in an aqueous phase of the system (for example, as described in U.S. Pat. No. 4,021,486 to Halasz et al.).

Emulsifiers may be used when the final form of the hair dye is to be an emulsion. Many emulsifiers are by their nature also surfactants. Illustrative general categories of emulsifiers include anionic, cationic, nonionic, amphoteric, fatty acid esters and sorbitan fatty acid esters. Examples include, but are not limited to, mono-, di-, and trialkyl ether phosphates, long-chain fatty acids with hydrophilic compounds such as glycerin, polyglycerin, or sorbitol, and long-chain alkyl primary and secondary amines, quaternary ammonium and quaternary pyridinium compounds.

The aqueous dyeing compositions of the present invention are prepared by conventional methods used in the hair dyeing art. Thus, they can be prepared by dissolving or suspending the dye in water in the desired concentrations. Water miscible organic solvents, e.g., aliphatic $C_1$–$C_4$ alcohols, such as ethanol or glycol ethers, can be employed to facilitate achieving solutions of the dye. In one embodiment, the dye can be dissolved first in the solvent and this solution is then diluted with water. The dispersion of the various ingredients can also be facilitated by heating the composition at temperatures varying from about 40° C. to 110°C., either before dilution with water or afterward. As a general guide, the concentrations of co-solvents or diluents are from about 5% to about 95%, depending upon storage, handling and application considerations.

It is also a common practice to add solvents or swelling agents to enhance the penetration of hair dyes. Materials useful for swelling hair include acetic acid, formic acid, formamide, urea, ethylamine and certain alkali halides (e.g., potassium iodide, sodium bromide, lithium bromide and lithium chloride. N-alkyl pyrrolidones and epoxy pyrrolidone may be employed potentially to increase the penetration of dye into hair. Imidazoles, such as disclosed in U.S. Pat. No. 5,030,629, may be employed in the compositions to enhance the penetration of hair dyes.

The present invention also provides a method for dyeing keratinous fibers, especially human hair, in which a composition according to the invention is applied to hair for its direct dyeing. For the direct dyeing method, the compositions of the invention are applied to hair by conventional techniques used in this art. Illustratively, when applied to living hair on the human head, the compositions of the invention can be applied to the hair with a brush, sponge, or other means of contact, such as pouring the composition directly onto the hair until saturated and/or manually massaging or working through the hair. The reaction time or time of contact of the dyeing composition with the hair is not critical and can vary over a wide range used in the hair dyeing art, such as for periods of from about 1 minute to about 2 hours. Preferably a period of from about 5 minutes to about 60 minutes is used; most preferably a period of from about 10 minutes to about 40 minutes is used.

The dyeing temperature can vary over wide limits as is conventional in this art. Thus, the dyeing temperature can range from about 20° C. to about 45° C. At the end of the time period, the composition is rinsed from the hair with water. If desired, a shampoo or a weak acid solution may also be employed.

In accordance with the present invention, the novel direct dyeing compositions may be applied to natural or dyed hair, permanently-waved hair, unpermed hair, or to hair which is highly or lightly bleached.

Other advantages and characteristics of the present invention will be apparent from the examples presented below, which are provided by way of illustration.

EXAMPLES

The following examples as set forth herein are meant to exemplify and illustrate the various aspects of carrying out the invention and are not intended to limit the invention in any way.

Example 1

To evaluate the dyeing properties of the mixtures of the invention on human hair, blended gray hair swatches and bleached hair were dyed with Mixture 1 of the present invention, which comprises about 10%-70% of 1-[(2-hydroxyethyl)amino-4-[(3-hydroxypropyl)amino]-9,10-anthracenedione and about 30%-90% of a combination of DB 23 and 1,4-bis[(3-hydroxypropyl)-amino]-9,10-anthracenedione. The swatches were also dyed with 1% DB 3a (Artisil Blue B) and with 1% DB 3b (Intrasperse Brilliant Blue B Supra). Artisil Blue B (Sandoz Corporation) and Intrasperse Brilliant Blue B Supra (Crompton & Knowles Corporation) are examples of two, commercially-available DB 3 dye preparations commonly used in hair dye formulations (see Table 1). The total amount of colorant used was the same for Mixture 1 of the present invention, DB 3a and DB 3b. Table 2 presents the results of the hair dyeing performance of Mixture 1 of the present invention compared with the hair dyeing performance of the commercial Disperse Blue 3a and 3b products.

TABLE 2

Hunter Values of Hair Swatches Dyed With Mixture 1 of the Present Invention and With Disperse Blues

| | Blended gray hair | | | Bleached hair | | | | |
|---|---|---|---|---|---|---|---|---|
| | L | a | b | L | a | b | ΔE | Δb |
| Undyed | 33.39 | −0.08 | 5.26 | 62.37 | 2.27 | 19.22 | | |
| Mixture 1 of the present invention | 25.58 | −0.49 | 1.65 | 30.52 | −3.42 | −14.15 | 46.67 | −33.37 |

TABLE 2-continued

Hunter Values of Hair Swatches Dyed With Mixture 1 of the Present Invention and With Disperse Blues

|  | Blended gray hair | | | Bleached hair | | | | |
|---|---|---|---|---|---|---|---|---|
|  | L | a | b | L | a | b | ΔE | Δb |
| DB 3a[+] | 29.06 | 0.47 | 1.26 | 32.77 | 1.76 | −10.31 | 41.81 | −29.53 |
| DB 3b[++] | 27.02 | −0.65 | 1.23 | 33.81 | −3.29 | −11.72 | 42.47 | −30.94 |

[+]Artisil Blue B (Sandoz Corporation)
[++]Intrasperse Brilliant Blue B Supra (Crompton & Knowles Corporation)

For these analyses, the hair was dyed for 30 minutes at room temperature with 1% dye in a commercial semi-permanent hair dye base. The swatches were then water-rinsed and air-dried. In order to remove any difference(s) that might have been due to effects of the hair dye base, the same hair dye base was employed in all of the tests.

The L values for the Mixture 1-dyed swatches show that these swatches are dyed the most intensely (i.e., the lower the L value, the darker the color). The results of this analysis are even more instructive when bleached hair is examined, since this substrate better demonstrates the effect of large anthraquinone molecules. The b (and Δb) and the L (and ΔE) values as presented in Table 2 demonstrate that Mixture 1 dyed bleached hair bluer and more intensely than either of the commercially available DB 3 products tested, i.e., the more negative the b value, the bluer the dyeing.

Example 2

The hair dyeing performance of the novel anthraquinone mixtures of the present invention was evaluated in combination with other anthraquinone dyes typically used in hair dyeing. As an illustrative example, Mixture 1 of the present invention was used in combination with Disperse Violet 1 (DV 1). Bleached hair was dyed for 30 minutes at room temperature with 1% Mixture 1 or DB 3a and 1% Intrasperse Red Violet RH New (Disperse Violet 1, Crompton & Knowles) in a commercial semi-permanent formulation. The hair was then water-rinsed and air-dried. The results are presented in Table 3.

TABLE 3

Hunter Values of Hair Swatches Dyed with Mixture 1 of the Present Invention + DV 1 versus Disperse Blue 3a* + DV 1

|  | L | a | b |
|---|---|---|---|
| Mixture 1 of the present invention + DV 1 | 26.55 | 6.80 | −21.18 |
| DB 3a* + DV 1 | 32.27 | 6.43 | −11.66 |

*Artisil Blue B (Sandoz Corporation)

Examination of the L and b values presented in Table 3 clearly shows significantly increased intensity and blueness of color by the Mixture 1+DV 1 combination versus the DB 3a+DV 1 combination. Thus, Mixture 1 was found to have a stronger synergistic dyeing effect than did DB 3 when used in combination with DV 1.

Example 3

A comparison of the relative hair dyeing performance of the novel anthraquinone mixtures of the present invention, Mixture 1 and Mixture 2, was performed. The results are presented in Table 4. Bleached hair was dyed for 30 minutes at room temperature with a direct dye formulation containing 1% Mixture 1 or 1% Mixture 2. The hair was then water-rinsed and air-dried.

TABLE 4

Hunter Values of Hair Swatches Dyed With Either Mixture 1 or Mixture 2 of the Present Invention

|  | Blended gray hair | | | Bleached hair | | |
|---|---|---|---|---|---|---|
|  | L | a | b | L | a | b |
| Mixture 1 | 37.34 | −3.79 | 1.73 | 40.38 | −10.61 | −1.6 |
| Mixture 2 | 39.69 | −1.93 | 4.71 | 47.12 | −6.45 | 7.05 |

The L values for the Mixture 1-dyed swatches show that these swatches are dyed more intensely than those dyed by Mixture 2 (i.e., the lower the L value, the darker the color). When bleached hair is examined as a substrate, a similar result is observed. A difference between Mixture 1's and Mixture 2's affinity for the hair is likely to account for the differences in the dyeing performance of each mixture for gray and bleached hair, as seen in Table 4.

The contents of all patents, patent applications, published articles, books, reference manuals and abstracts cited herein are hereby incorporated by reference in their entirety to more fully describe the state of the art to which the invention pertains.

As various changes can be made in the above-described subject matter without departing from the scope and spirit of the invention, it is intended that all subject matter contained in the above description, shown in the accompanying drawings, or defined in the appended claims be interpreted as descriptive and illustrative, and not in a limiting sense. Many modifications and variations of the present invention are possible in light of the above teachings. It is therefore to be understood that within the scope of the appended claims, the invention may be practiced otherwise than as specifically described.

What is claimed is:

1. An anthraquinone mixture comprising three different anthraquinone compounds, said compounds having the formula:

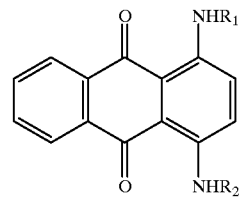

wherein $R_1$ and $R_2$ are, independently, monohydroxy $C_2$–$C_6$ alkyl, straight chain or branched chain, with the proviso that in two of the anthraquinones, $R_1$ and $R_2$ are the same, and as a consequence, such anthraquinones are symmetric, and in the third of the anthraquinones, $R_1$ and $R_2$ differ, and as a consequence, such an anthraquinone is asymmetric; wherein said two symmetric anthraquinone compounds in combination are present in said mixture in an amount of about 30% to about 90% by weight, based on the total weight of the mixture; and wherein said asymmetric anthraquinone is present in said mixture in an amount of about 10% to about 70% by weight, based on the total weight of the mixture.

2. The mixture according to claim 1, wherein said asymmetric anthraquinone compound comprises about 25% to about 65%, by weight, based on the total weight of said mixture and each of said symmetric anthraquinone compounds comprises about 3% to about 70%, by weight, based on the total weight of said mixture.

3. The mixture according to claim 1, wherein said asymmetric anthraquinone compound comprises about 30% to about 60% of said mixture and each of said symmetric anthraquinone compounds comprises about 5% to about 50% of said mixture.

4. The mixture according to claim 1, wherein $R_1$ and $R_2$ are independently selected from the group consisting of 2-hydroxyethyl, 2-hydroxypropyl, 3-hydroxypropyl, hydroxybutyl, hydroxypentyl and hydroxyhexyl.

5. A composition comprising the anthraquinone mixture according to claim 1 in a tinctorially effective amount for coloring a keratin fiber, the mixture being in a cosmetically acceptable vehicle.

6. A composition comprising the anthraquinone mixture according to claim 2 in a tinctorially effective amount for coloring a keratin fiber, the mixture being in a cosmetically acceptable vehicle.

7. The mixture according to claim 1, wherein said anthraquinone compounds are 1,4-bis[(2-hydroxyethyl)amino]-9,10-anthracenedione, 1-[(2-hydroxyethyl)amino-4-[(3-hydroxypropyl)amino]-9,10-anthracenedione and 1,4-bis[(3-hydroxypropyl)amino]-9,10-anthracenedione.

8. The mixture according to claim 1, wherein said anthraquinone compounds are 1,4-bis[(2-hydroxyethyl)amino]-9,10-anthracenedione, 1-[(2-hydroxyethyl)amino]-4-[(2-hydroxypropyl)amino]-9,10-anthracenedione and 1,4-bis[(2-hydroxypropyl)amino]-9,10-anthracenedione.

9. The mixture according to claim 1, wherein said anthraquinone compounds are 1,4-bis[(2-hydroxypropyl)amino]-9,10-anthracenedione, 1-[(2-hydroxypropyl)amino]-4-[(3-hydroxypropyl)amino]-9,10-anthracenedione and 1,4-bis[(3-hydroxypropyl)amino]-9,10-anthracenedione.

10. A method of dyeing a keratin hair fiber comprising contacting said hair fiber with a tinctorially effective amount of the mixture according to claim 1 in a cosmetically acceptable vehicle, said contacting being for a time sufficient to dye said fiber.

11. A method of dyeing a keratin hair fiber comprising contacting said hair fiber with a tinctorially effective amount of the mixture according to claim 2 in a cosmetically acceptable vehicle, said contacting being for a time sufficient to dye said fiber.

* * * * *